United States Patent
Coomans

(10) Patent No.: US 8,066,686 B2
(45) Date of Patent: Nov. 29, 2011

(54) DIAPER FASTENER

(75) Inventor: Michel Coomans, Ham (BE)

(73) Assignee: Avery Dennison Corporation, Pasadena, CA (US)

( * ) Notice: Subject to any disclaimer, the term of this patent is extended or adjusted under 35 U.S.C. 154(b) by 788 days.

(21) Appl. No.: 11/916,309

(22) PCT Filed: May 19, 2006

(86) PCT No.: PCT/US2006/019363
§ 371 (c)(1),
(2), (4) Date: Dec. 3, 2007

(87) PCT Pub. No.: WO2006/138016
PCT Pub. Date: Dec. 28, 2006

(65) Prior Publication Data
US 2008/0195076 A1    Aug. 14, 2008

Related U.S. Application Data

(60) Provisional application No. 60/697,172, filed on Jul. 7, 2005, provisional application No. 60/690,951, filed on Jun. 16, 2005.

(51) Int. Cl.
*A61F 13/15* (2006.01)
*A61F 13/20* (2006.01)

(52) U.S. Cl. ............... 604/386; 604/385.29; 604/385.3; 604/387; 604/388; 604/389; 604/390

(58) Field of Classification Search ............... 604/386, 604/385.29, 385.3, 387, 388, 389, 390
See application file for complete search history.

(56) References Cited

U.S. PATENT DOCUMENTS

| | | | |
|---|---|---|---|
| 3,748,701 A | | 7/1973 | De Mestral |
| 3,930,503 A | * | 1/1976 | Tritsch ......................... 604/389 |
| 4,169,303 A | | 10/1979 | Lemelson |
| 4,522,853 A | * | 6/1985 | Szonn et al. ................. 428/40.1 |
| 4,726,971 A | | 2/1988 | Pape et al. |
| 4,778,701 A | | 10/1988 | Pape et al. |
| 4,801,480 A | * | 1/1989 | Panza et al. ................. 428/41.9 |

(Continued)

FOREIGN PATENT DOCUMENTS

EP    0148587    12/1984

(Continued)

OTHER PUBLICATIONS

PCT/US2006/019363; PCT International Search Report dated Oct. 6, 2006.

*Primary Examiner* — Melanie Hand
*Assistant Examiner* — Ginger T Chapman

(57) ABSTRACT

A fastener (10) comprising an attachment section (30) for permanent attachment to an anchoring area, a target section (60) for permanent attachment to a landing area, and a fastening section (40) for selective attachment and detachment from the target section (60). A breakable connection (70) initially connects the fastening section (40) and the target section (60), and this connection (70) is broken to disconnect the fastening section (40) from the target section (60) when fastener (10) is converted from a closed condition to an opened condition. A single fingerlift (80) can be gripped both when converting the fastener (10) from an installed condition to the closed condition, and when converting the fastener (10) from the closed condition to the opened condition.

13 Claims, 10 Drawing Sheets

U.S. PATENT DOCUMENTS

| | | | |
|---|---|---|---|
| 5,026,446 | A | 6/1991 | Johnston et al. |
| 5,053,028 | A | 10/1991 | Zoia et al. |
| 5,106,383 | A | 4/1992 | Mulder et al. |
| 5,158,557 | A | 10/1992 | Noreen et al. |
| 5,182,156 | A | 1/1993 | Pape et al. |
| 5,234,517 | A | 8/1993 | Pape et al. |
| 5,510,161 | A | 4/1996 | Lloyd |
| 5,537,722 | A | 7/1996 | Niederhofer et al. |
| 5,554,146 | A | 9/1996 | Niederhofer et al. |
| 5,571,097 | A | 11/1996 | Seth |
| 5,599,601 | A | 2/1997 | Polski et al. |
| 5,722,969 | A | 3/1998 | Ito et al. |
| 6,363,587 | B1 | 4/2002 | Richter et al. |
| 6,485,478 | B2 | 11/2002 | Imai et al. |
| 6,764,480 | B2 | 7/2004 | Tani et al. |
| 2004/0249357 | A1 | 12/2004 | Michielsen et al. |

FOREIGN PATENT DOCUMENTS

| | | |
|---|---|---|
| EP | 0336639 | 10/1993 |
| EP | 0752239 A1 * | 7/1996 |
| EP | 0832631 | 9/1997 |
| EP | 0832630 | 4/1998 |
| EP | 0853935 | 7/1998 |
| EP | 0941730 | 3/1999 |
| EP | 1000598 | 11/1999 |
| EP | 1449505 | 2/2003 |
| FR | 2380771 | 9/1978 |

\* cited by examiner

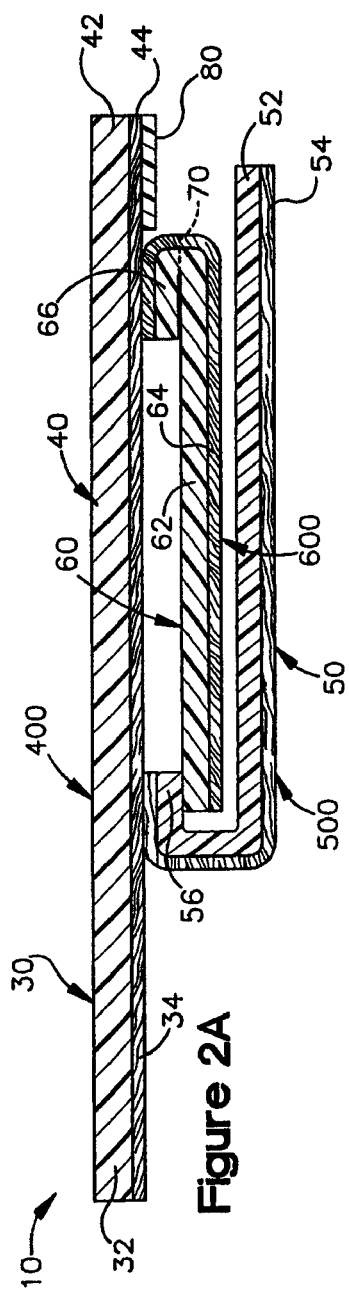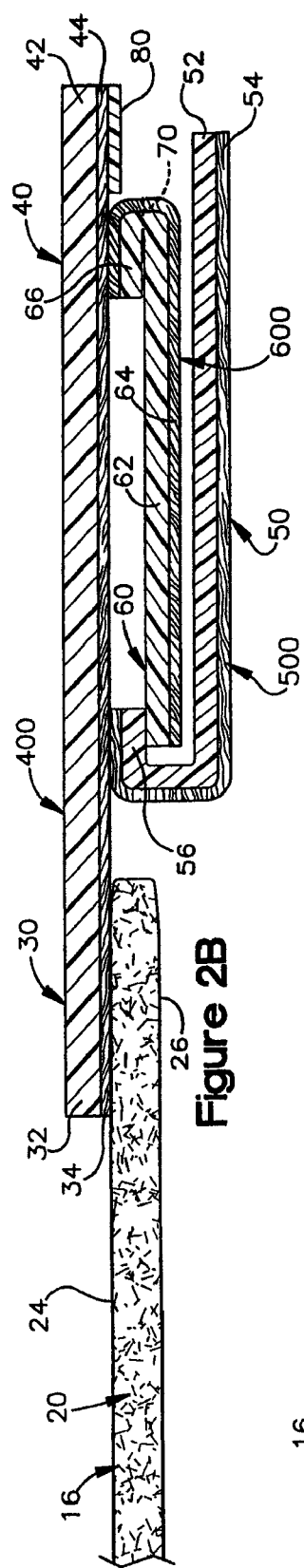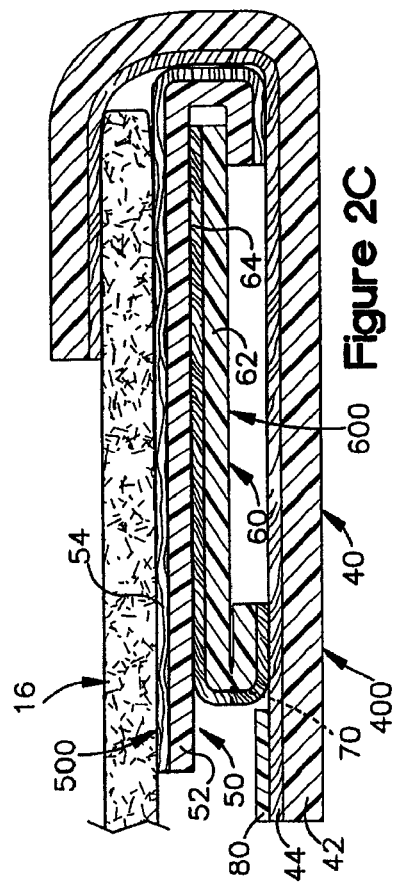

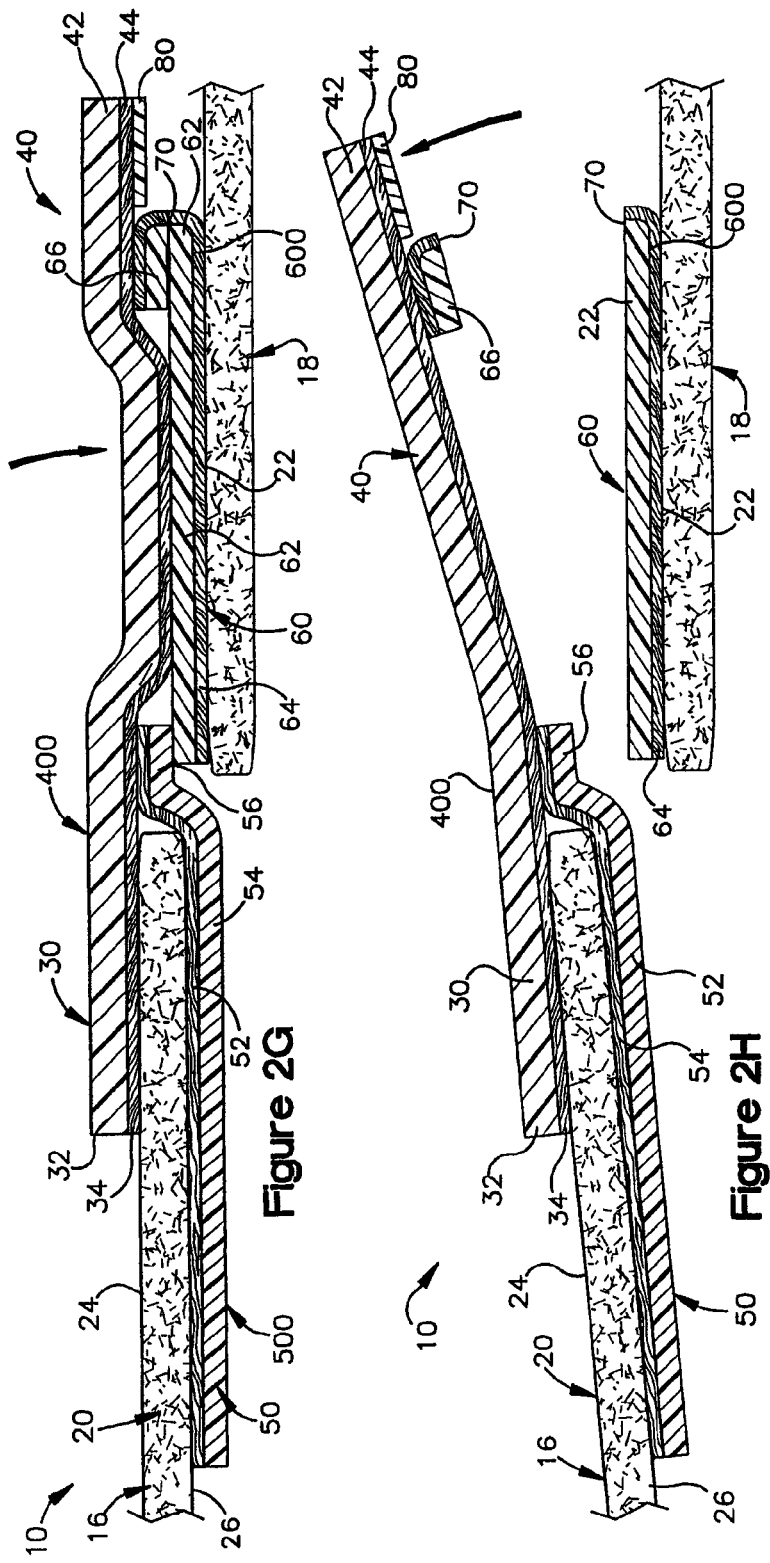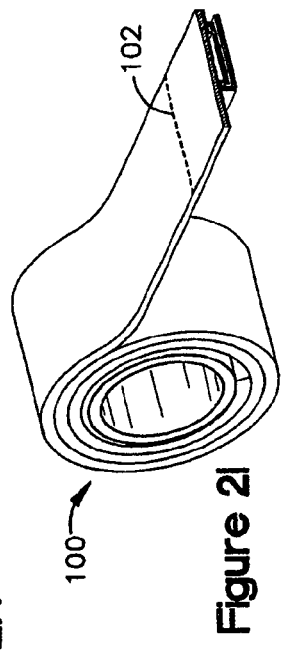

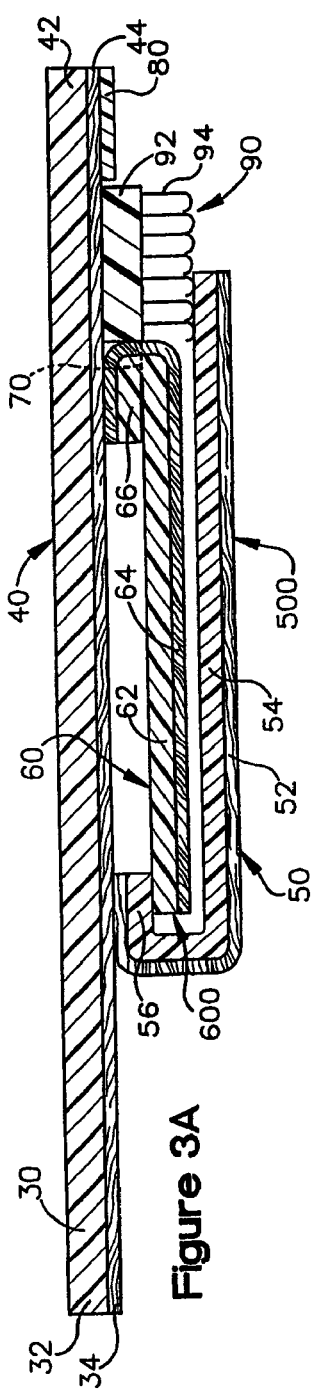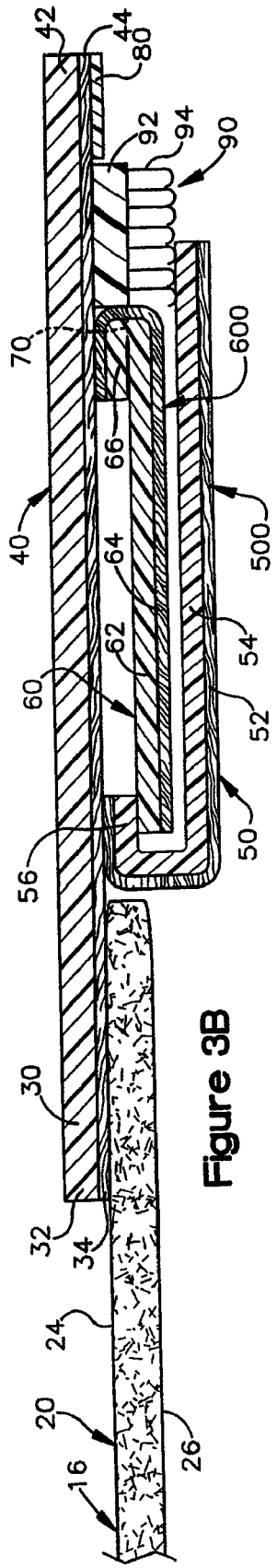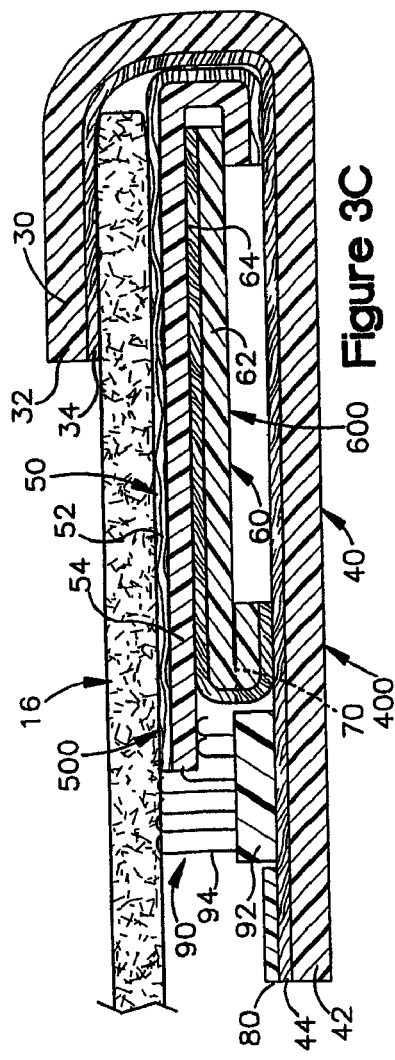

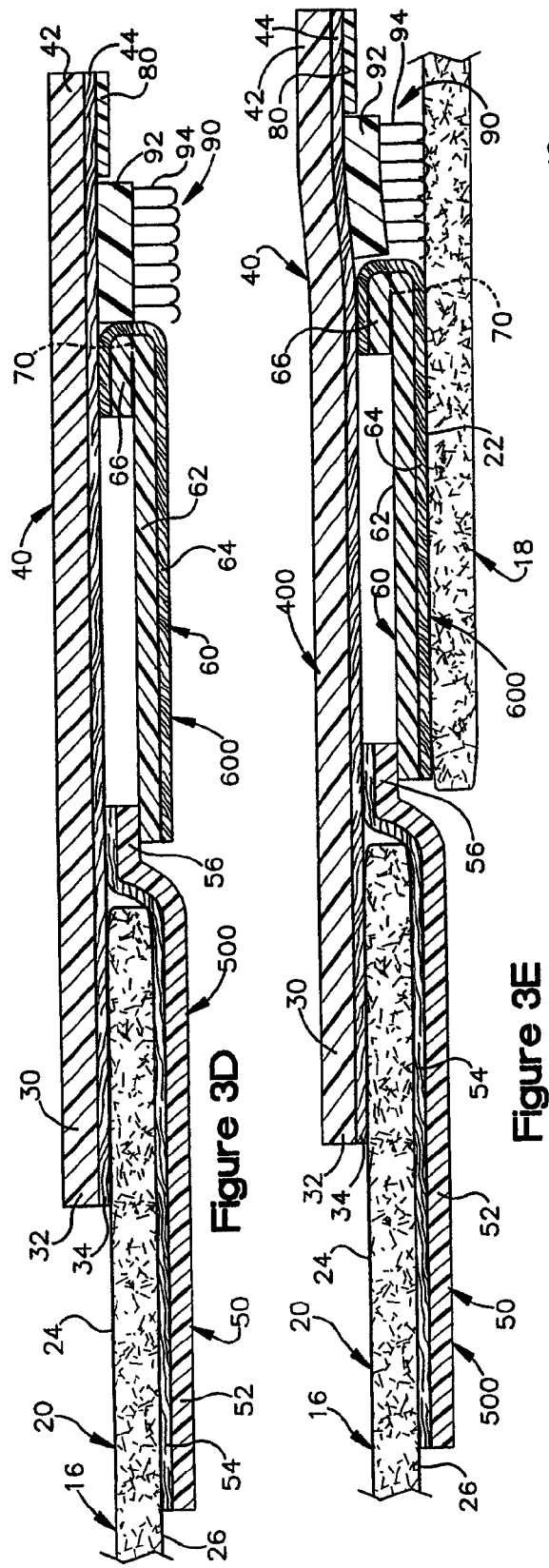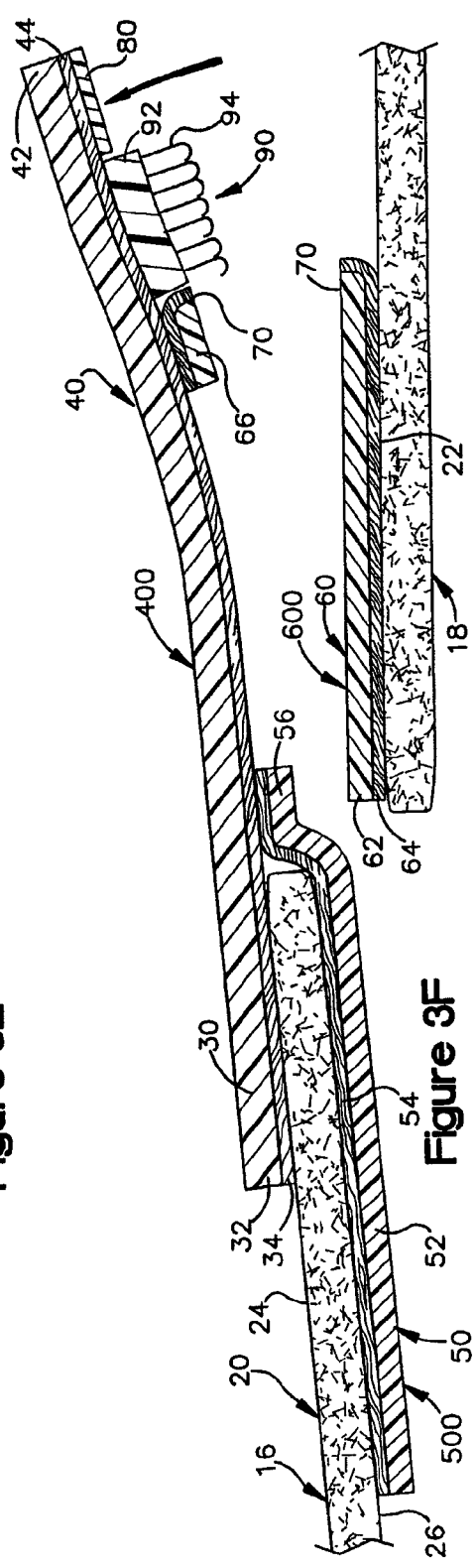
Figure 3D
Figure 3E
Figure 3F

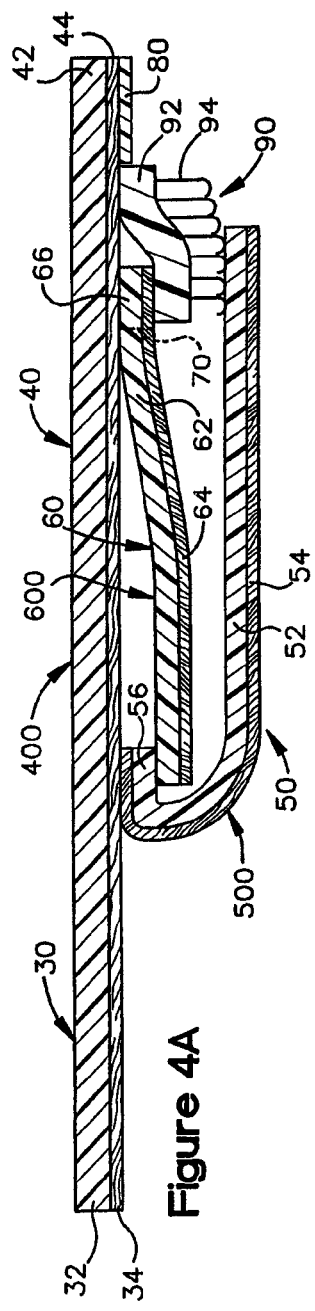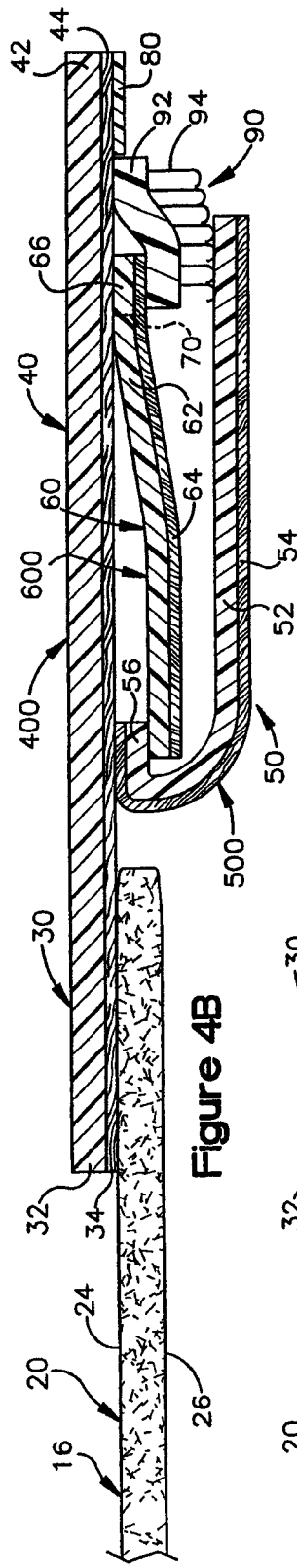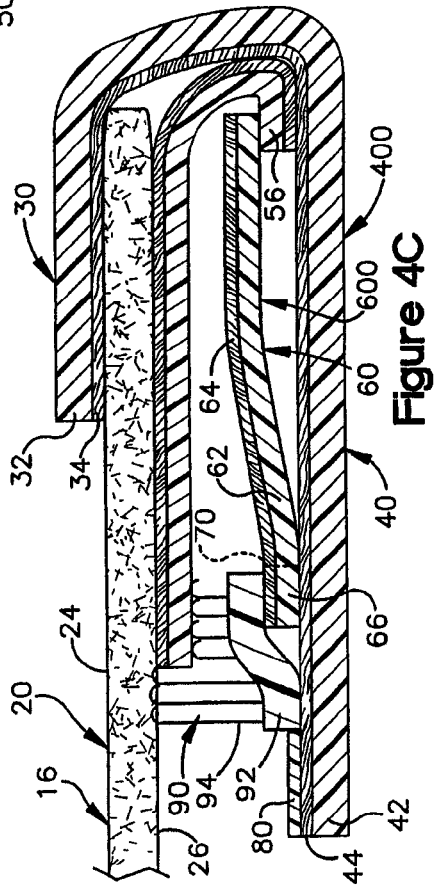

DIAPER FASTENER

This application is a national phase of International Application No. PCT/US2006/019363, filed May 19, 2006, which claims priority to U.S. Provisional Application Ser. No. 60/697,172, filed Jul. 7, 2005, which claims priority to U.S. Provisional Application Ser. No. 60/690,951, filed Jun. 16, 2005. The entire disclosure of this international application and the entire disclosure of these provisional applications are hereby incorporated by reference.

FIELD OF THE INVENTION

This invention relates generally to a diaper fastener comprising a target section that a user permanently attaches to a landing area on the diaper and a fastening section that is releasably attached to the target section so that the user can reopen and reclose the fastener.

BACKGROUND OF THE INVENTION

A disposable diaper can comprises a laminate having a liquid absorbent pad enclosed within a liquid permeable inner shell and a liquid impermeable outer shell. The diaper has a rear portion and a front portion. Fasteners can be attached to edges of the rear portion and arranged to provide closure about the wearer upon engagement with respective landing areas on the front portion of the diaper. Each diaper fastener can be convertible from an installed condition, to a deployed condition, and to a closed condition. If the diaper fasteners are reopenable, they can each also be converted from the closed condition to an opened condition, and then between a reclosed condition and a reopened condition.

A reopenable diaper fastener can comprise an outer attachment section, an inner attachment section, a target section, and a fastening section. The attachment sections are intended to be permanently attached, by the diaper manufacturer, to the outer and inner surfaces, respectively, of the edge of the rear portion of the diaper. The target section is intended for permanent attachment, by a user, to the landing area on the front portion of the diaper. The fastening section is initially releasably attached to the target section and is intended to be unattached and reattached, by a user, to open, reclose and reopen the fastener.

A diaper fastener will also typically include a first fingerlift attached to the target section and a second, different fingerlift attached to the fastening section. The first fingerlift is gripped by the user when converting the fastener from the installed condition to the closed condition. The second different fingerlift is gripped by the user when opening, reclosing, and reopening the fastener.

SUMMARY OF THE INVENTION

The present invention provides a fastener wherein the fastening section is initially connected to the target section and disconnected from the target section when the fastener is converted from the closed condition to the opened condition. This connection/disconnection allows, among other things, a fastener design wherein a single fingerlift can be gripped by a user both when converting the fastener from the installed condition to the closed condition, and when converting the fastener from the closed condition to the opened condition (and between the reclosed and reopened conditions). It may be noted that with the conventional two-fingerlift design, the user may accidentally grip and pull the wrong fingerlift when attempting to accomplish a desired conversion. For example, if the user accidently grips and pulls the target section's fingerlift when attempting to open (or reopen) the fastener, the target section can be torn from the diaper making further use of the fastener impractical and/or impossible. With the single-fingerlift design allowed by the present invention, there is no user confusion as to which fingerlift should be gripped when initially closing the fastener and/or to which fingerlift should be gripped when opening (and reclosing and reopening) the fastener.

More particularly, the present invention provides a fastener convertible from an installed condition, to a deployed condition, and then to a closed condition, and, once in the closed condition, convertible to an opened condition and, once in the opened condition, convertible between a re-closed condition and a re-opened condition. The fastener comprises an attachment section, a target section, and a fastening section. The attachment section is for permanent attachment to a surface of an anchoring area when the fastener is in the installed condition and conditions thereafter. The target section is for permanent attachment to a landing area when the fastener is in the closed condition and conditions thereafter. The fastening section is connected to the target section when the fastener is in conditions prior to the opened condition; disconnected from the target section when fastener is converted from the closed condition to the opened condition, and attachable to and from the target section when the fastener is converted between the re-closed condition and the re-opened condition.

The connection/disconnection of the fastening section to the target section can be accomplished by a breakable connection therebetween. The breakable connection can comprise, for example, a designed weakness (e.g. a perforated line) in the target section. Upon pulling the fastening section to convert the fastener from the closed position to the opened position, the designed weakness allows a controlled breaking away from the target section. A small section of the target section may break-away with the fastening section during this conversion.

The connection, and selective disconnection, of the fastening section and the target section allows the fastener to have a single fingerlift. The fingerlift can be gripped when converting the fastener from the installed condition to the closed condition, and when converting from the fastener from the closed condition to the opened condition. This same fingerlift can also be gripped for conversion of the fastener between the reclosed condition and the reopened condition. The fingerlift can occupy a distal gripping area so that it remains accessible and grippable throughout the use of the fastener.

These and other features of the invention are fully described and particularly pointed out in the claims. The following description and drawings set forth in detail certain illustrative embodiments of the invention. These embodiments are indicative of but a few of the various ways in which the principles of the invention may be employed.

DRAWINGS

FIGS. 2A-2H are side views of the fastener in a pre-installation condition, a partially installed condition, a completely installed condition, a deployed condition, a closed condition, an opened condition, a reopened condition, and a reclosed condition.

FIG. 2I is a perspective view of a roll which can be laterally cut at intervals corresponding to the desired width of the fasteners to provide a plurality of the fasteners.

FIGS. 3A-3H are side views of the fastener in a pre-installation condition, a partially installed condition, a completely installed condition, a deployed condition, a closed condition, an opened condition, a reopened condition, and a reclosed condition.

FIGS. 4A-4H are side views of the fastener in a pre-installation condition, a partially installed condition, a completely installed condition, a deployed condition, a closed condition, an opened condition, a reopened condition, and a reclosed condition.

DETAILED DESCRIPTION

Figure 1:
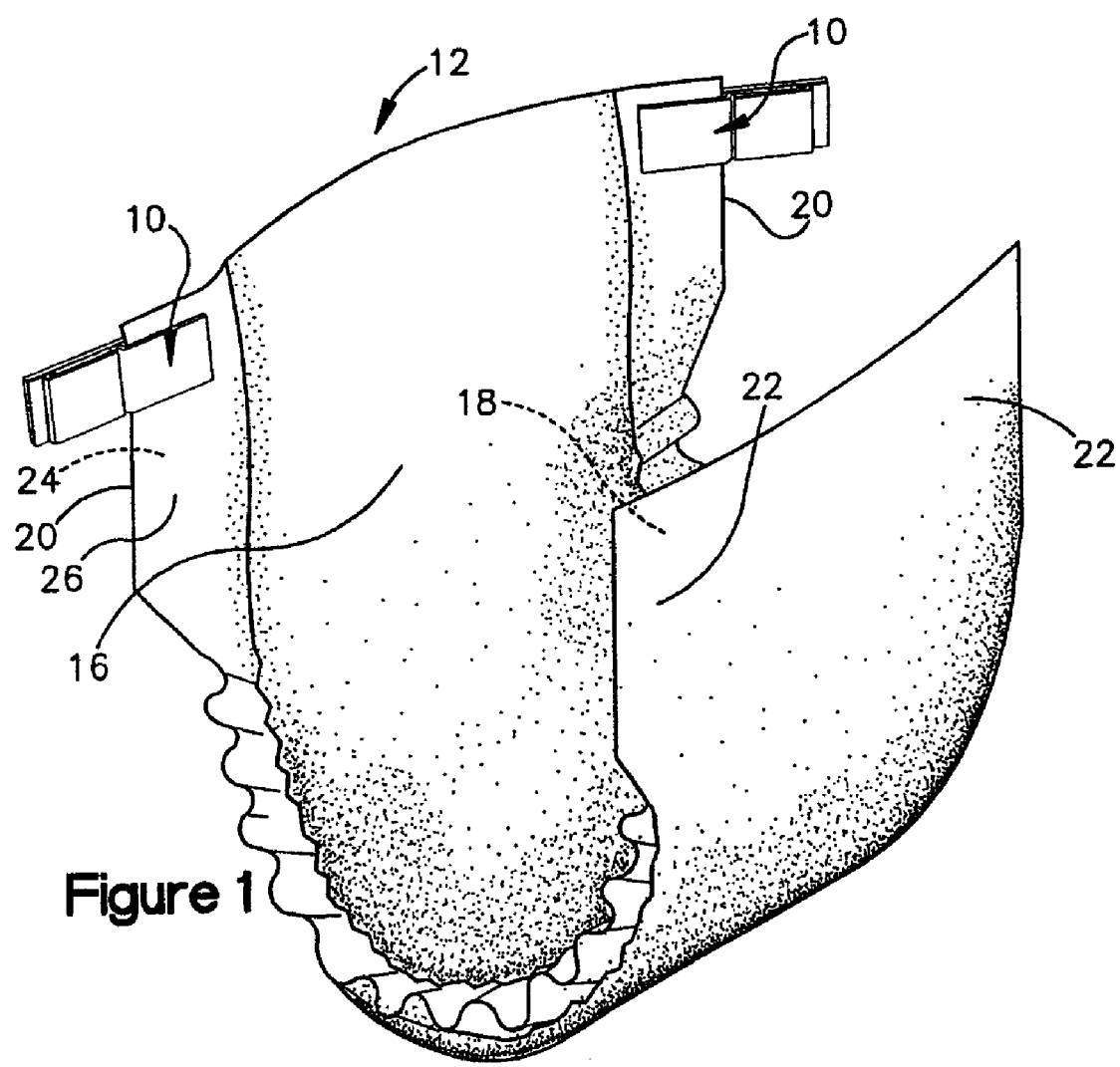
FIG. 1 is a perspective view of a disposable diaper with a pair of fasteners according to the present invention.

Referring now to the drawings, and initially to FIG. 1, a pair of fasteners 10 according to the present invention are shown installed, and in a deployed condition, on a disposable diaper 12. The illustrated disposable diaper 12 comprises a laminate having a liquid absorbent pad enclosed within a liquid permeable inner shell and a liquid impermeable outer shell. The diaper 12 has a rear portion 16 which is intended to cover the wearer's behind and a front portion 18 which is intended to cover the wearer's front. The fasteners 10 are respectively attached to edges 20 of the rear portion 16 and are arranged to provide closure about the wearer upon engagement with respective landing areas 22 on the front portion 18 of the diaper. The edges 20 can be viewed as having an outer surface 24 and an inner surface 26.

Referring now to FIGS. 2A-2H, the fastener 10 is shown in a pre-installation condition, a partially installed condition, a completely installed condition, a deployed condition, a closed condition, an opened condition, a reopened condition, and a reclosed condition, respectively. The fastener 10 comprises an attachment section 30, a fastening section 40, another attachment section 50, and a target section 60. The fastener 10 also includes a breakable connection 70 between the fastening section 40 and the target section 60. As is explained in more detail below, this breakable connection 70 allows the fastener 10 to have a single fingerlift 80 that can be gripped both to convert the fastener 10 from the installed condition to a deployed condition and to convert the fastener 10 from a closed condition to a re-opened condition.

In the illustrated embodiment, a first tape strip 400 (sometimes called the fastener tape) forms the attachment section 30 and the fastening section 40, a second tape strip 500 (sometimes called the release tape) forms the attachment section 50, and a third tape strip 600 (sometimes called the target tape) forms the target section 60. However, other constructions of the sections 30/40/50/60 are certainly possible with and contemplated by, the present invention. For example, the attachment section 30 and the fastening section 40 could comprise separate distinct strips. Additionally or alternatively, the attachment section 50 and/or the target section 60 could have multi-piece strip constructions.

It should be noted that the thicknesses of the sections 30/40/50/60 and the tapes 400/500/600 are greatly exaggerated for ease of explanation. The thicknesses of these sections/tapes will usually be in the range of, for example, about 5 to about 100 microns. If these thicknesses were drawn to scale with the illustrated lengths of the sections 30/40/50/60 and the tapes 400/500/600, it would be more difficult to decipher and/or number the various sections/tapes of the fastener 10. Thus, the exaggerated thicknesses in the drawings are provided to more clearly show the arrangement of these sections/tapes when the fastener 10 is in the various conditions.

In the pre-installation condition (FIG. 2A) and illustrated orientation, the attachment section 30 comprises a substrate 32 having an adhesive layer 34 on its bottom surface, the fastening section 40 comprises a substrate 42 having an adhesive layer 44 on its bottom surface, the attachment section 50 comprises a substrate 52 having an adhesive layer 54 on its bottom surface, and the target section 60 comprises a substrate 62 and an adhesive layer 64 on its bottom surface. The attachment section 30 and the fastening section 40 are coextensive with each other. The major portions of the attachment section 50 and the target section 60 are positioned parallel to the coextensive sections 30/40, with the target section 60 being positioned between the fastening section 40 and the attachment section 50.

In the illustrated embodiment, the attachment section 30 and the fastening section 40 are formed from the first tape strip 400. Accordingly, the substrates 32 and 42 are actually one continuous substrate and the adhesive layers 34 and 44 can appear to be (or may actually be) one continuous adhesive layer. The sections 30 and 40 define the overall length of the fastener 10 which, for disposable diaper applications, is usually in the range of 40 mm to 100 mm.

Figure 4D:
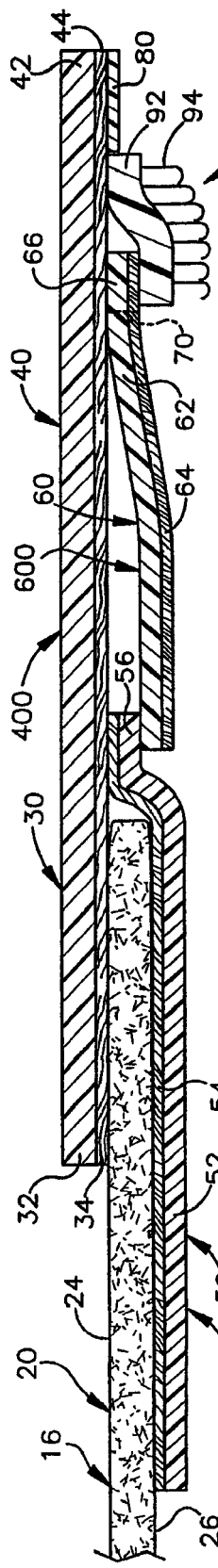
Figure 4E:
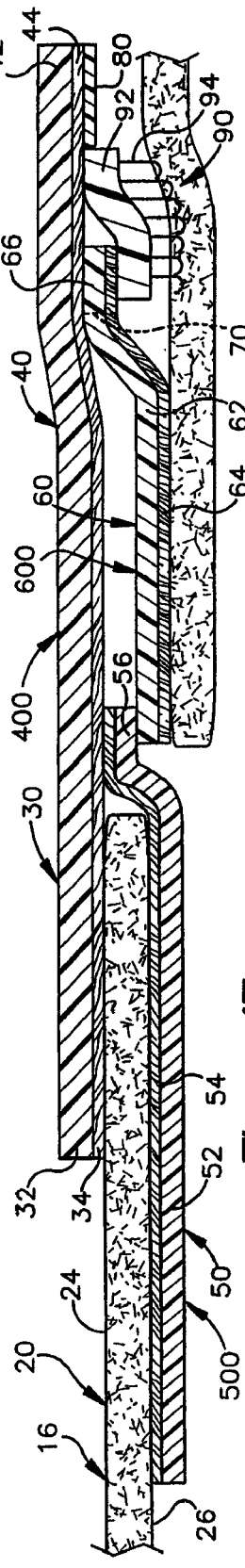

The substrate 52 of the attachment section 50 has a generally rectangular strip shape and is folded in a manner corresponding to the elongated J-shape shown in the drawings in an exaggerated fashion. The upper surface of the tail 56 of the J-shape is connected to the first tape 400 (via the adhesive layer 44 and the adhesive layer 54) and defines the division between the attachment section 30 and the fastening section 40. This geometry of the attachment section 50 results in a Y-shaped bond being formed around the diaper edge 20 (which is often referred to in the industry as a Y-bond) when the fastener 10 is in its deployed condition (FIG. 4D) and conditions thereafter (FIGS. 4E-4H).

The substrate 62 of the target section 60 has a generally rectangular plan shape with a folded outer end forming a tab 66 which, as is explained in more detail below, is a breakaway tab. The upper surface of the other end of the substrate 62 positioned adjacent to (but not connected to), the bottom surface of the tail 56 of the substrate 52. The breakable connection 70 is positioned in between the tab 66 and the rest of the target section 60, and in the illustrated embodiment, comprises perforations in the substrate 62. The fingerlift 80 is positioned on the distal lower surface of the substrate 42 of the fastening section 40 and fills a space aligned between the edge of the target section 60 and the edge of the fastening section 40.

The fastener 10 can be provided to the diaper manufacturer in the "flat" pre-installation condition (FIG. 2A). As is best seen by referring briefly to FIG. 2I, a plurality of the fasteners 10 in the pre-installation condition can be cut from a stock roll 100, preferably in a high-speed efficient manufacturing manner. The width of the roll 100 corresponds to the desired length of the fasteners 10 and the distance of the cut line 102 corresponds to their desired width. Although not specifically shown in the drawings, the attachment section 30 and/or the fastening section 40 can include a release coating on the upper surface of their substrates 30 and 40 to prevent "blocking" when the fastener material is in this roll form.

The diaper manufacturer can install the fastener 10 onto rear edge 20 of the diaper 12 and the user can receive the diaper 12 with fasteners in the installed condition. To install the fastener 10, the attachment section 30 is permanently secured to the outer surface 24 of the diaper's edge 20 by the adhesive 34. (FIG. 2B.) The fastening section 40, the attachment section 50, and the target section 60 are then pivoted in the clockwise direction and the attachment section 50 is permanently attached (via its adhesive layer 54) to the inner surface 26 of the diaper edge 20. (FIG. 2C.)

In the installed condition (FIG. 2C), the target tape 60 is temporarily attached (via its adhesive layer 64) to the non-adhesive surface of the substrate 52 of the attachment section 50. The fastening section 40 is connected to the target section 60 via the breakable connection 70 (and is also temporarily attached, via its adhesive layer 44, to the non-adhesive surface of the target substrate 62). The fingerlift 80 extends beyond the attachment section 50 and the target section 60 for convenient gripping.

Figure 2D:
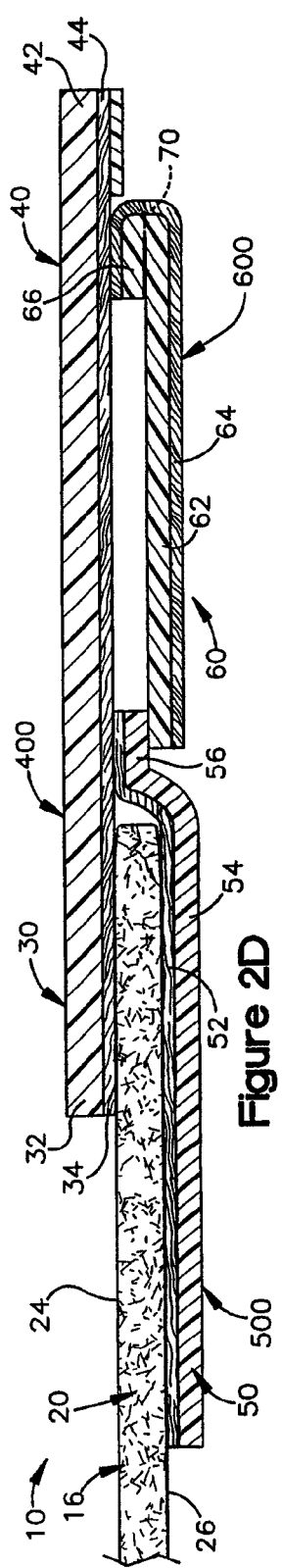
Figure 2E:
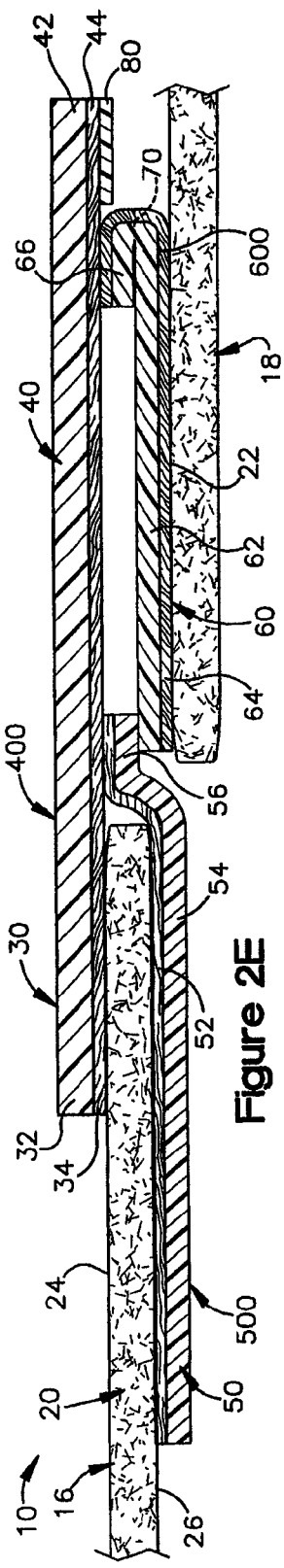

The fastener 10 is convertible from the installed condition (FIG. 2C) to the deployed condition (FIG. 2D) and then to the closed condition (FIG. 2E). To deploy the fastener 10, the fingerlift 80 is gripped and the fastening section 40 (with the target section 60 connected thereto by the breakable connection 70) is pivoted in the counterclockwise direction. (FIG. 2D.) The target section 60 is permanently attached, via its adhesive layer 64, to the landing area 22 of the front portion of the diaper 12 (which has previously been fitted over the wearer). (FIG. 2E.) The fastening section 40 is still connected to the target section 60 via the breakable connection 70 (and is also temporarily attached, via its adhesive layer 44, to the non-adhesive surface of the target substrate 62). The fingerlift 80 extends beyond the target section 60 for convenient gripping.

Figure 2F:
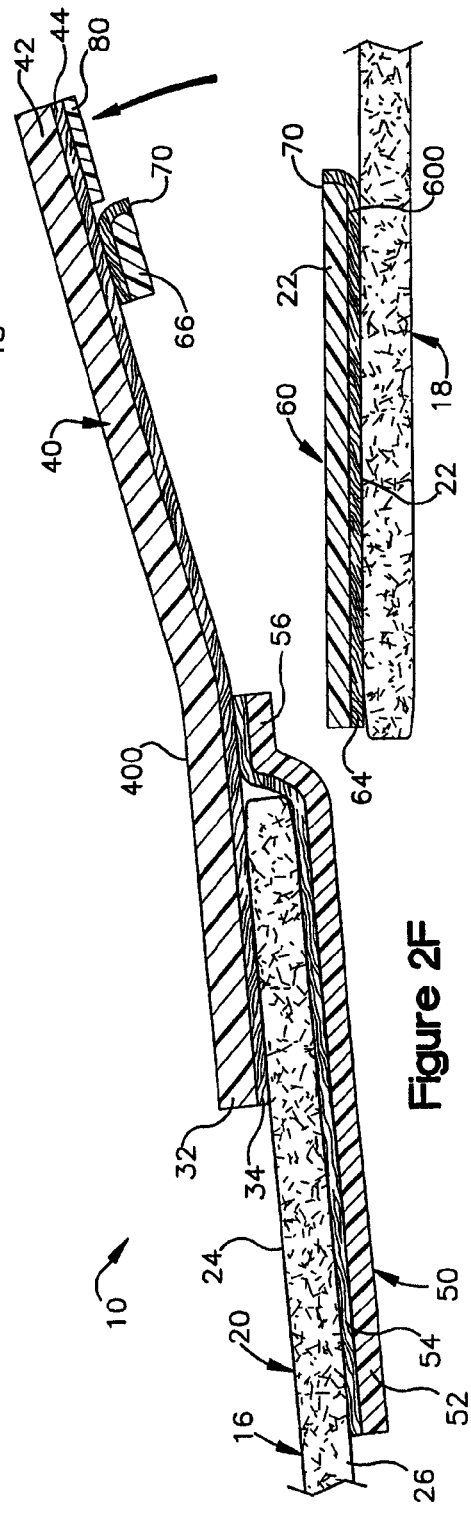

Once the fastener 10 is in the closed condition (FIG. 2E), it is convertible to the opened condition (FIG. 2F). To convert to the opened condition, the fingerlift 80 is grasped and the fastening section 40 is pivoted counterclockwise back toward the attachment section 30. This movement results in the connection 70 being broken and the fastening section 40 disconnecting from the target section 60, which is permanently attached to the landing area 22. The breakaway tab 66 of the target section 60 can remain with the fastening section 40 after this disconnection.

Once the fastener 10 is in the opened condition (FIG. 2F), it is convertible between the re-closed condition (FIG. 2G) and the re-opened condition (FIG. 2H), simply by pivoting the fastening section 40 (now disconnected from the target section 60) towards and away from the target section 60. In the re-closed condition (FIG. 2G), the adhesive layer 44 releasably attaches the fastening section 40 to the target section 60.

Accordingly, the attachment section 30 is permanently attached to a surface (e.g., the outer surface 24) of an anchoring area (e.g., the rear diaper edge 20) when the fastener 10 is in the installed condition and conditions thereafter. The fastening section 40 is connected to the target section 60 when the fastener is in conditions prior to the opened condition, is disconnected from the target section 60 when the fastener 10 is converted from the closed condition to the opened condition. Additionally, the fastening section 40 is attachable to and from the target section 60 when the fastener 10 is converted between the re-closed condition and the re-opened condition. The attachment section 50 is permanently attached to another surface (e.g., the inner surface 26) of the anchoring area 20 when the fastener 10 is in the installed condition and conditions thereafter. The target section 60 is releasably attached to the attachment section 50 when the fastener 10 is in the installed condition, is removed from the attachment section 50 when the fastener 10 is in the deployed condition and conditions thereafter, and is permanently attached to a landing area 22 when the fastener 10 is in the closed condition and conditions thereafter.

As for the breakable connection 70, it is intact when the fastener 10 is in conditions up to and including the closed condition. The connection 70 is broken during the conversion of the fastener 10 between the closed condition and the opened condition, and thus is broken when the fastener 10 is in the reclosed condition and the reopened condition.

Significantly, the single fingerlift 80 can be gripped both when converting the fastener 10 from the installed condition (FIG. 2D) to the closed condition (FIG. 2F) and when converting the fastener 10 from the closed condition (FIG. 2F) to the opened condition (FIG. 2G). (The fingerlift 80 can also be gripped when converting the fastener 10 between the reclosed condition and the reopened condition.) Thus, there is no user confusion as to which fingerlift should be gripped when initially closing the fastener 10 (i.e., converting the fastener 10 from the installed condition to the closed condition) and/or to which fingerlift should be gripped when opening the fastener 10 (i.e., converting the fastener 10 from the closed condition to the opened or reopened condition). In the installed condition (FIG. 2D), the closed condition (FIG. 2F), the reopened condition (FIG. 2G), and the reclosed condition (FIG. 2H), the fingerlift 80 occupies the distal portion of the gripping area of the fastener 10, whereby it remains accessible and grippable throughout the use of the fastener.

Referring now to FIGS. 3A-3H, a modified form of the fastener 10 is shown, this fastener 10 having a hook section 90. The hook section 90 comprises a substrate 92 and hooks 94 extending outward from a bottom surface thereof. (The thickness of the substrate 92 and/or the height of the hooks 94 is exaggerated somewhat in the drawings for ease in explanation and/or to accommodate the exaggerated thicknesses of the fastener sections 30/40/50/60.) As shown in FIG. 3I, a plurality of the fasteners 10 in the pre-installation condition (FIG. 3A), can be cut from a stock roll 100.

Figure 3G:
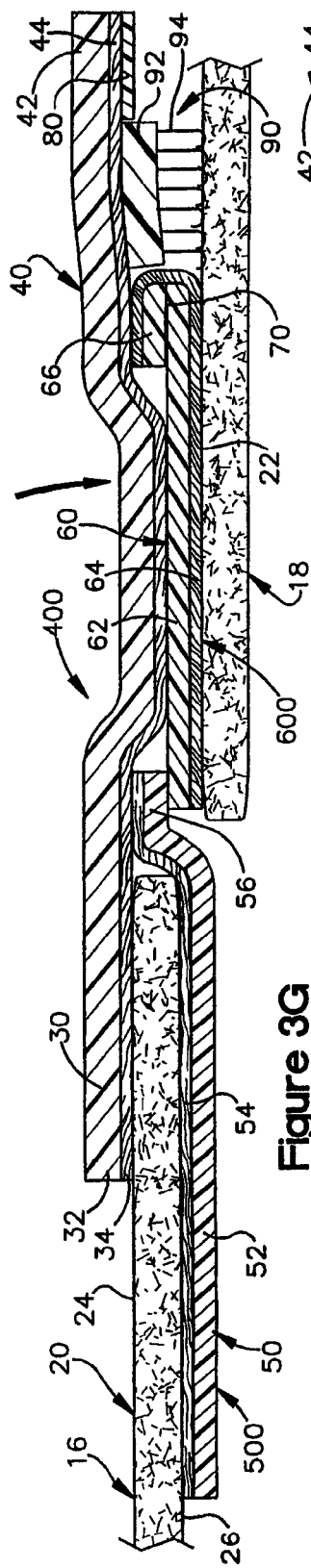
Figure 3H:
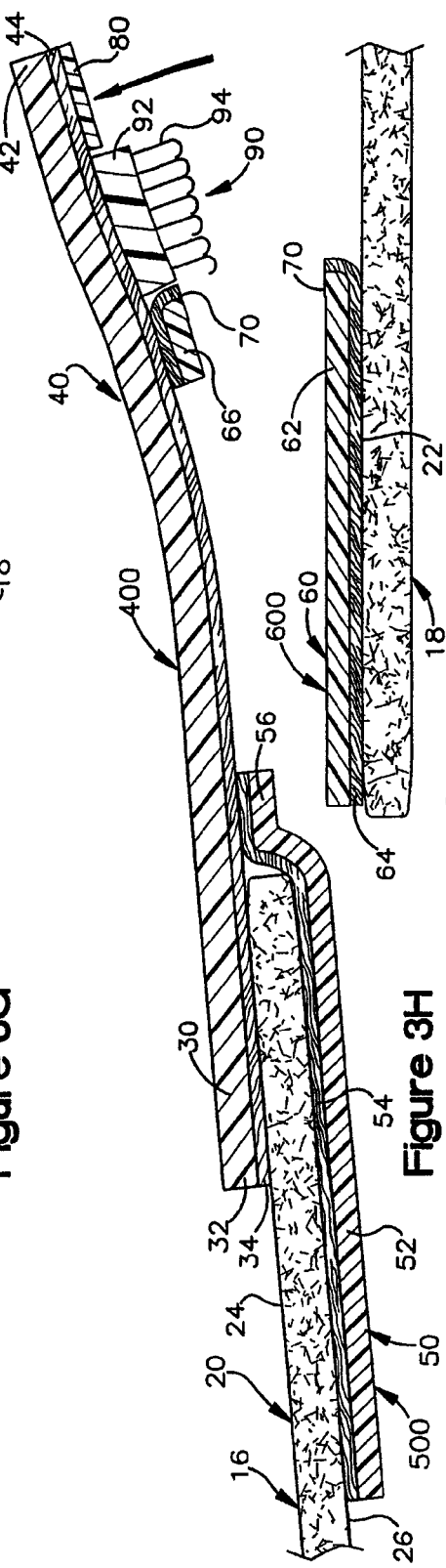
Figure 3I:
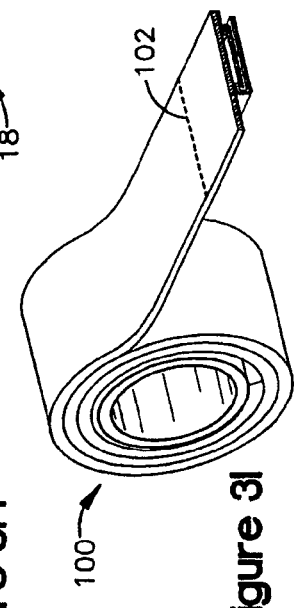
FIG. 3I is a perspective view of a roll which can be laterally cut at intervals corresponding to the desired width of the fasteners to provide a plurality of the fasteners.

In the fastener 10 shown in FIGS. 3A-3H, the hook section 90 is attached to the fastening section 40 (via the adhesive 44) and is positioned between the edge of the fingerlift 80 and the edge the target section 60. Thus, in this embodiment, the fingerlift 80 and the hook section 90 fill a space aligned between the edge of the target section 60 and the edge of the fastening section 40. The hooks 94 releasably attach to the inner diaper surface 24 when the fastener 10 is in the installed condition (FIG. 3C), releasably attach to the front diaper portion 18 when the fastener 10 is in the closed or reclosed condition (FIG. 3E and FIG. 3G), and remain attached to the fastening section 40 after the connection 70 is broken (FIG. 3F-FIG. 3H).

Figure 4F:
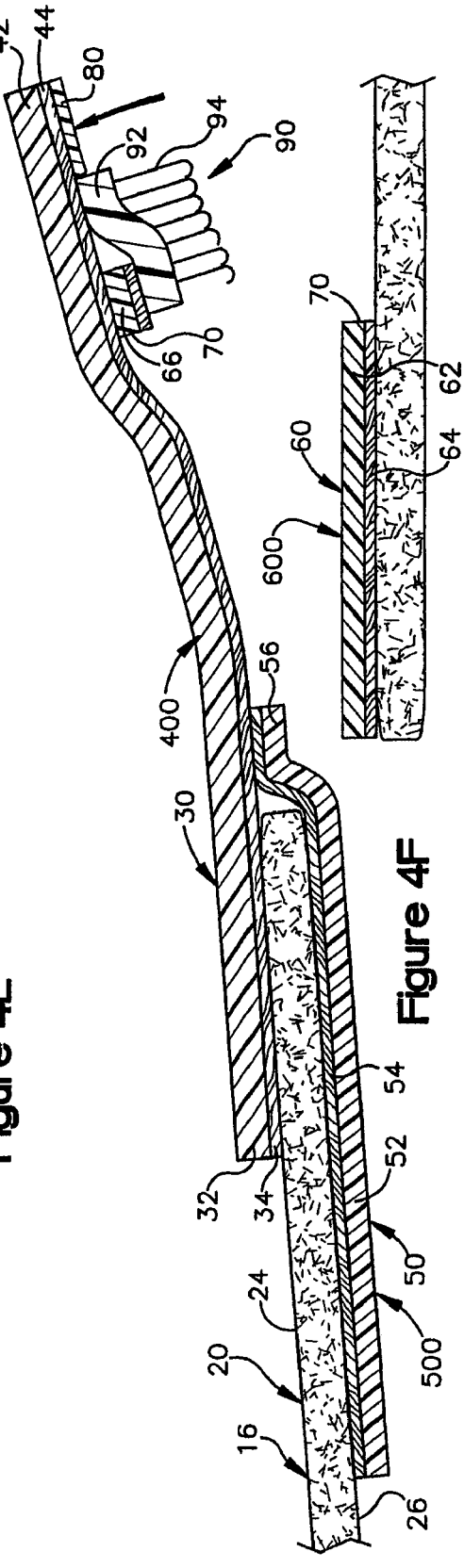
Figure 4G:
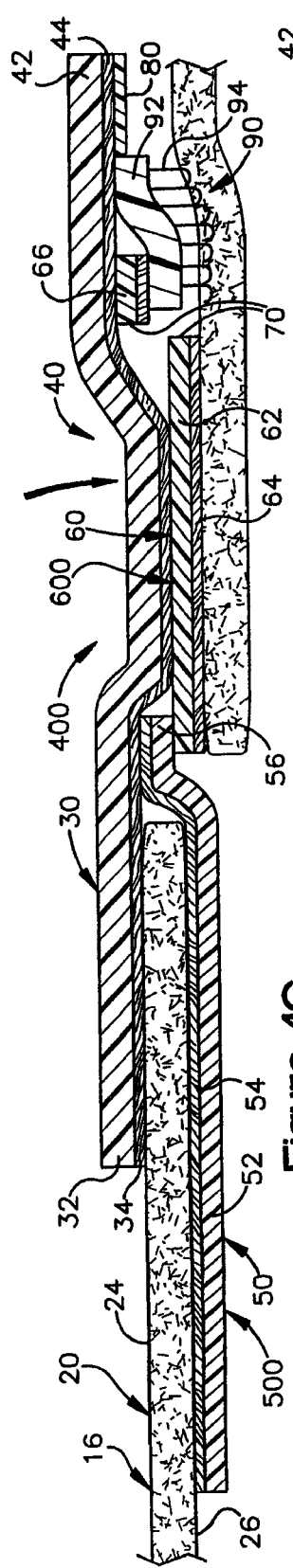
Figure 4H:
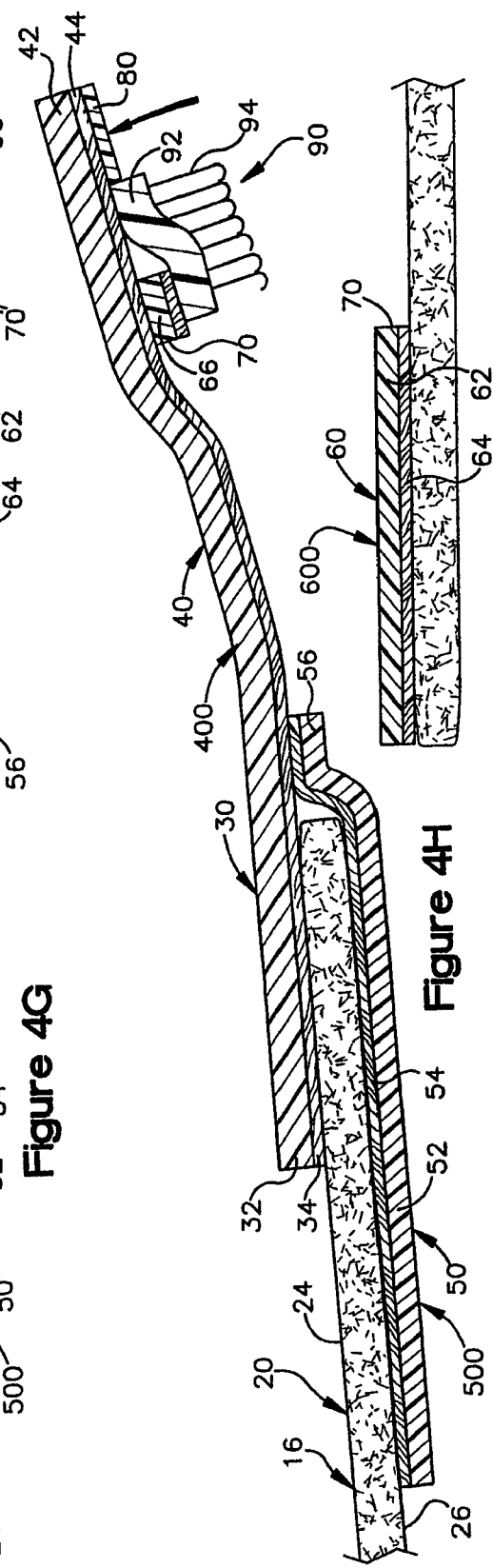
Figure 4I:
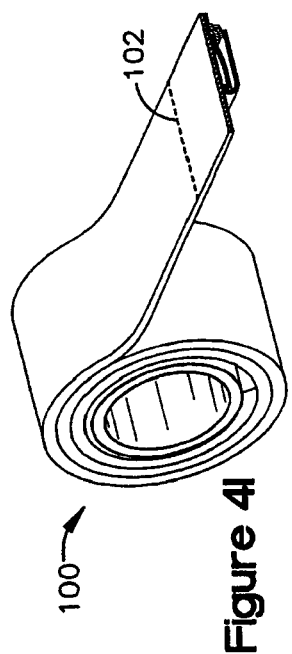
FIG. 4I is a perspective view of a roll which can be laterally cut at intervals corresponding to the desired width of the fasteners to provide a plurality of the fasteners.

Referring now to FIGS. 4A-4H, another modified form of the fastener 10 is shown, this fastener 10 also having a hook section 90. In this embodiment, the breakaway tab 66 of the target section 60 is not folded over and breakable connection 70 defines its inner edge. The hook section 90 is attached to the target section 60 (via the adhesive 44) outward of the breakable connection 70, and is aligned to be inward from the inner edge of the fingerlift 80. The hooks 94 releasably attach to the inner diaper surface 24 when the fastener 10 is in the installed condition (FIG. 4C), releasably attach to the front diaper portion 18 when the fastener 10 is in the closed or reclosed condition (FIG. 4E and FIG. 4G), and again remain attached to the fastening section 40 after the connection 70 is broken (FIG. 4F-FIG. 4H). As shown in FIG. 4I, a plurality of the fasteners 10 in the pre-installation condition (FIG. 4A), can be cut from a stock roll 100.

The substrates 32, 42, 52, and 62 can be made of cloth, kraft paper, cellophane film, non-woven webs, polymeric films (e.g., polypropylene, polyvinyl chloride, polyethylene terephthalate, and polyethylene) or other suitable materials or laminates. The fingerlift 80 can be made of the same or similar substrate materials.

The adhesive layers 34, 44, 54, 64, can be any conventional adhesive, including pressure sensitive adhesives and non-pressure sensitive adhesives. Suitable pressure sensitive adhesives include acrylic resin and natural or synthetic based rubber adhesives. The layers 34 and 54 can comprise permanent adhesives as they are used to permanently attached the attachment sections 30 and 50 to the diaper edge 20. The layer 44 can comprise a releasable adhesive for selective attachment to and detachment of the fastening section 40 to the target section 60. The layer 64 can comprise an adhesive which can permanently secure the target section 60 to the landing area 22 and also temporarily attach the target section to the attachment section 50. (A release coating can be used on the non-adhesive surface of the attachment substrate 52 to accomplish this permanent/temporary function.) It may be noted, however, that non-adhesive means (e.g., thermal bonds, magnetic connections, sonic bonds, mechanical connectors, etc.) could be used instead for any or all of the attaching/fastening adhesives for the sections 30, 40, 50 and 60.

The release coatings can be a silicone coating, a carbamate coating, or any other coating which promotes detachment of the relevant adjacent section when unwinding the stock roll 100 and/or converting the fastener 10 between conditions.

The hook substrate 92 and the hooks 94 may be separately formed and subsequently attached (by, for example, embedding, adhesives, etc.) or may be integrally formed (by, for example, stamping, molding, etc.). The hooks 94 may have any "hooking" form such as, for example, a J-shape geometry, a mushroom-shape geometry, an arrow-shape geometry, a barbed geometry, a bulbous geometry, etc. (See e.g., U.S. Pat. Nos. 3,748,701 and 4,169,303.) If the hook section 90 is used, the landing area 22 and/or the diaper inner surface 26 can have complimentary loops which do not interfere with the adhesive (or other) attachment of the target section 60 to the landing area 22 and/or the attachment section 50 to is the diaper surface 26. Often, however, the fibrous nature of the diaper material will allow it to alone function as an engaging surface for the hooks 94.

It may now be appreciated that the present invention provides a fastener 10 wherein the fastening section 40 is initially connected to the target section 60 and disconnected therefrom when the fastener 10 is converted from the closed condition to the opened condition. This connection/disconnection allows a fastener design wherein a single fingerlift 80 can be gripped by a user both when converting the fastener 10 from the installed condition to the closed condition, and when converting the fastener 10 from the closed condition to the opened condition. Unlike with conventional two-fingerlift designs, there is no user confusion as to which fingerlift should be gripped when initially closing the fastener 10 and/or to which fingerlift should be gripped when opening (or reopening) the fastener 10.

Although the invention has been shown and described with respect to certain preferred embodiments, it is obvious that equivalent and obvious alterations and modifications will occur to others skilled in the art upon the reading and understanding of this specification. For example, although the invention is shown in connection with a disposable diaper for a wearer, the fastener 10 may be employed with non-disposable diapers and/or non-diaper absorbent articles. In fact, the fastener 10 could find application in situations not even remotely involving absorbent articles. The present invention includes all such alterations and modifications and is limited only by the scope of the following claims.

The invention claimed is:

1. A fastener convertible from an installed condition on an article, to a deployed condition, and then to a closed condition, and, once in the closed condition, convertible to an opened condition and, once in the opened condition, convertible between a re-closed condition and a re-opened condition; said fastener comprising:

an attachment section for permanent attachment to a surface of an anchoring area on a first portion of the article, when the fastener is in the installed condition and conditions thereafter, a target section for permanent attachment to a landing area on another portion of the article, when the fastener is in the closed condition and conditions thereafter, a fastening section connected to the target section when the fastener is in conditions prior to the opened condition; disconnected from the target section when fastener is converted from the closed condition to the opened condition, and attachable to and from the target section when the fastener is converted between the re-closed condition and the re-opened condition;

a breakable connection between the fastening section and the target section which is broken to disconnect the fastening section from the target section when fastener is converted from the closed condition to the opened condition; and a single fingerlift that can be gripped when converting from the installed condition to the closed condition, and when converting from the closed condition to the opened condition.

2. A fastener as set forth in claim 1, wherein the breakable connection comprises perforations in the target section.

3. A fastener as set forth in claim 1, wherein the target section includes a breakaway tab which remains with the fastening section when fastener is converted from the closed condition to the opened condition.

4. A fastener as set forth in claim 1, wherein the fingerlift occupies a distal gripping area whereby it remains accessible and grippable throughout the use of the fastener.

5. A fastener as set forth in claim 1, wherein the fingerlift is positioned in a space aligned between an edge of the fastening section and an edge of the target section.

6. A fastener as set forth in claim 1, wherein the attachment section and the fastening section are coextensive with each other.

7. A fastener as set forth in claim 6, wherein the attachment section and the fastening section are formed from a single tape strip.

8. A fastener as set forth in claim 7, wherein the combined length of the attachment section and the fastening section defines the length of the fastener in a pre-installation condition.

9. A fastener as set forth in claim 7, further comprising another attachment section for permanent attachment to another surface of the anchoring area on the first portion of the article, when the fastener is in the installed condition and conditions thereafter.

10. A fastener as set forth in claim 9, wherein, when the fastener is in a pre-installation condition, major portions of the attachment section and the target section are positioned parallel to the coextensive sections, with the target section being positioned between the fastening section and the attachment section.

11. A fastener as set forth in claim 10, wherein the attachment section has a geometry such that a Y-shaped bond is formed around an edge of the anchoring area when the fastener is in the closed condition and conditions thereafter.

12. A fastener as set forth in claim 11, wherein the target section is releasably attached to the attachment section in the installed condition, with the fastening section still connected to the target section.

13. A fastener as set forth in claim 1, further comprising a hook section connected to either the fastening section or the target section.

* * * * *